United States Patent
Voelkel

(10) Patent No.: US 6,906,802 B2
(45) Date of Patent: Jun. 14, 2005

(54) SYSTEM FOR ANALYZING SAMPLE LIQUIDS CONTAINING A POSITION CONTROL UNIT

(75) Inventor: Dirk Voelkel, Heidelberg (DE)

(73) Assignee: Roche Diagnostic Operations, Inc., Indianapolis, IN (US)

( * ) Notice: Subject to any disclaimer, the term of this patent is extended or adjusted under 35 U.S.C. 154(b) by 110 days.

(21) Appl. No.: 10/008,600

(22) Filed: Dec. 4, 2001

(65) Prior Publication Data

US 2002/0167668 A1 Nov. 14, 2002

(30) Foreign Application Priority Data

Dec. 8, 2000 (DE) .......................................... 100 61 336

(51) Int. Cl.$^7$ .............................................. G01N 21/47
(52) U.S. Cl. .................................... 356/446; 422/82.05
(58) Field of Search ................. 356/39, 446; 422/82.05

(56) References Cited

U.S. PATENT DOCUMENTS

| | | | |
|---|---|---|---|
| 5,246,858 A | | 9/1993 | Arbuckle et al. |
| 5,424,035 A | | 6/1995 | Hones et al. .................. 422/55 |
| 5,526,120 A | * | 6/1996 | Jina et al. ..................... 356/446 |
| 5,605,838 A | * | 2/1997 | Backhaus et al. ............. 436/34 |
| 5,801,817 A | * | 9/1998 | Riedel ........................ 356/4.07 |
| 6,036,919 A | | 3/2000 | Thym et al. .................... 422/58 |
| 6,055,060 A | | 4/2000 | Bolduan et al. ............. 356/433 |

FOREIGN PATENT DOCUMENTS

| | | | | |
|---|---|---|---|---|
| EP | 0234579 B1 | 9/1987 | .......... | G01N/21/55 |
| EP | 0618443 B1 | 10/1994 | .......... | G01N/21/86 |
| EP | 0779983 B1 | 6/1997 | .......... | G01N/33/52 |
| EP | 0819943 A2 | 1/1998 | .......... | G01N/35/10 |
| JP | 63-40840 | 2/1988 | | |

OTHER PUBLICATIONS

Beckmann, Petr et al, "The Scattering of Electromagnetic Waves from Rough Surfaces", Pergamon Press, Oxford London, New York, Paris, 1963 . (3 pgs).
European Search Report for European Application No. 01128869.3–1524–, Apr. 5, 2003, 4 pages.

* cited by examiner

*Primary Examiner*—Richard A. Rosenberger
(74) *Attorney, Agent, or Firm*—Barnes & Thornburg LLP

(57) ABSTRACT

System for analyzing sample liquids by evaluating test elements with an analytical unit (20) in which a test element (10) to be analyzed is positioned by a holder (21, 22, 120, 140) in an analytical position relative to the analytical unit and the system additionally comprises a position control unit to check whether an analytical area of the test element is correctly positioned relative to the analytical unit wherein the position control unit comprises a light source (30, 2) to irradiate an area of the test element and preferably the analytical area (11), a detector (31, 131) to detect light reflected from the area and an evaluation unit, and the light source and detector are positioned relative to one another in such a manner that the light intensity of specularly reflected radiation at the detector when the test element is correctly positioned is different from a light intensity when it is incorrectly positioned and the evaluation unit recognizes any faulty positioning on the basis of the light intensity at the detector.

Figure 1:
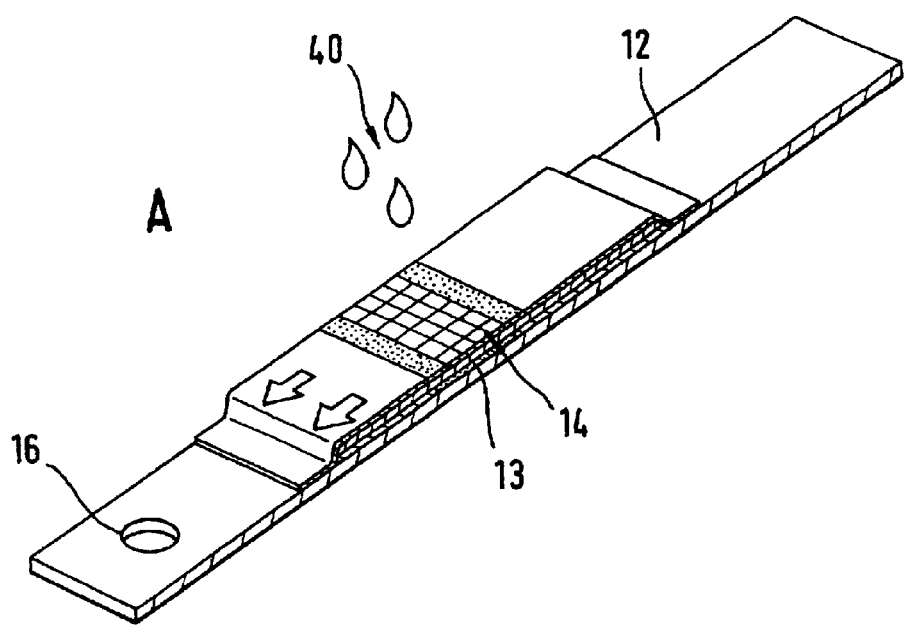
Figure 1:
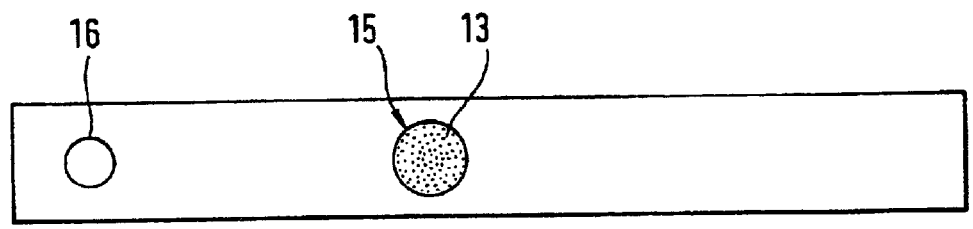

In addition the invention concerns a method for sample analysis using a position control unit to check whether a test element is correctly positioned relative to an evaluation optics.

14 Claims, 5 Drawing Sheets

A

B

A

B

A                    B

1mm

5mm

SYSTEM FOR ANALYZING SAMPLE LIQUIDS CONTAINING A POSITION CONTROL UNIT

The present invention relates to the field of sample liquid analysis by the use of analyte-specific, disposable test elements. The invention can be used in analytical systems in which the positioning of the test element relative to an evaluation unit is critical as is in particular the case for an optical evaluation of test elements.

Analytical systems which use disposable test elements are now commonly used in the prior art especially to determine the blood sugar level. These instruments are used by diabetics to monitor their blood sugar level which then provides a basis to adjust their eating habits or insulin dosage. In this field there are so-called sensor measuring instruments in which blood glucose is determined on the basis of an electrochemical measurement and optical systems in which an analyte-dependent colour change on the test element is used to determine the analyte concentration. Such optical systems which are based on an analyte-dependent colour change are also known for the evaluation of urine test strips or of test elements for other parameters such as lactate, creatinine, protein, uric acid, leucocytes etc. The relative positioning of the analytical area relative to the optical evaluation system is of decisive importance for the precision and accuracy of the measurement especially in the case of optical systems. Hence in the field of analytical systems for evaluating test elements, several attempts have been made to ensure that the analytical area of a test element is correctly positioned. Since the test elements are inserted in the instrument by the user in the case of relatively small analytical systems, the system must be simple to operate as well as allow a reliable positioning in order to make the system attractive for the user. A holder which meets these requirements and nevertheless has a simple construction is described in EP B 0 618 443. With this holder the test strip which has a recess at its front end (distal end) is pushed into the holder until a pin engages in the recess and positions the test strip longitudinally. The holder has guide elements in order to position the test strip in the transverse direction. Since the test element is held in an elevated position in the area of the pin and is pressed down by a pressure element, it adopts a slightly bent shape which presses the analytical area of the test element onto the support due to the flexibility of the test strip. A window or opening is located below the analytical area to allow an optical evaluation through this opening or through the window. However, even with a perfected holder like that described in EP 0 618 443 it is still possible for the user to lift the side (proximal end) of the test element that faces away from the holder in such a manner that it alters the positioning of the analytical area relative to the analytical instrument and the analytical result is falsified. This problem occurs to a greater extent in less-well developed test strip holders. Such incorrect positioning results in faulty measurements. These faulty measurements can have fatal consequences especially in the field of self monitoring of blood sugar by diabetics. If for example the user is led to believe that the blood sugar level is too high, he may react by injecting an excessive dose of insulin which in extreme cases can lead to a fatal hypoglycaemia. Hence there is an urgent need to be able to avoid the described faulty positioning or at least to be able to detect a faulty positioning so that the user can be made aware of the error.

According to the invention this object is achieved by a system for analysing sample liquids by evaluating test elements with an analytical unit in which a test element to be analysed is positioned by a holder in an analytical position relative to the analytical unit and the system has a position control unit which can be used to determine whether an analytical area of the test element is positioned correctly relative to the analytical unit. The position control unit has a light source to irradiate an area of the test element, preferably the analytical area, and a detector to detect light reflected from the area. The light source and detector are positioned relative to one another such that the light intensity of specularly reflected radiation at the detector is different when the test element is correctly positioned than when it is incorrectly positioned and a possible false positioning can be detected with an evaluation unit on the basis of the light intensity at the detector. In a first embodiment of such a system the light source and detector are positioned relative to one another in such a manner that the radiation of the light source that is specularly reflected from the test element falls on the detector when the test element is correctly positioned. If in contrast the test element is moved out of the correct position for example by lifting the end of the test element facing away from the holder, the light cone of the specularly reflected radiation moves such that it now does not directly fall on the detector and the light intensity at the detector decreases. In a second embodiment the converse procedure is chosen i.e. specularly reflected radiation never falls on the detector when the positioning is correct. If, however, a false positioning occurs the light cone of specularly reflected radiation impinges on the detector which in turn enables detection of the incorrect position.

Hence an analytical system with a position control unit according to the invention offers the user the advantage that erroneous analytical results can be avoided by detection of a faulty positioning. It is also possible to indicate to the user that the positioning is faulty so that he can remedy the situation and then reliably carry out the analysis with the same test element. Hence this embodiment avoids the user having to use a new test element which would give rise to costs and is disadvantageous for handling reasons since the user has to withdraw a new liquid sample (usually by pricking the finger pad).

The present invention can be used advantageously in analytical systems in which a faulty positioning of a test element leads to a falsification of analytical results. These are primarily optically measuring systems in which the analysis is carried out by irradiating an analytical area of the test element and evaluating reflected or transmitted radiation. Another preferred field of application is the field of relatively small analytical systems which are operated by the patient himself. Such a system is described for example in the document EP B 0 618 443. Such instruments are commercially available for example under the names Accutrend®, Accu Check®, Glucotrend® and Glucometer®. The invention is of particular importance in those systems in which test elements are used that can be bent along their longitudinal axis and which are only held at one end by the analytical instrument. The importance of the latter criterion becomes particularly apparent when the present invention is compared with the document EP B 0 779 983. In the instrument according to EP B 0 779 983 a test strip holder is used in which the test strip is held at its distal end as well as in an area which is proximal to the analytical area. This prevents the test strip from bending along its longitudinal axis in the region of the analytical area and thus also prevents faulty positioning that may result therefrom. However, the price that has to be paid for this is quite high with regard to user comfort. On the one hand insertion of the test element into the holder is relatively complicated and, on the other hand, the analytical area wetted with the sample liquid (usually blood) has to be pushed through a tapered position. The latter leads to a contamination of the test strip holder which is why the holder used in the system has to be designed to be removable for cleaning purposes. In contrast test element holders are used within the scope of the present invention in which the test element is only held at its distal end and the remaining region of the test element is freely accessible from the upper side. This gives the user the convenience of being able to simply insert the test element in the holder, and if desired by the user, the sample liquid can also be applied when the test element has already been correctly positioned in the analytical instrument for an analysis. This accessibility of the test element also gives a very open appearance to the analytical instrument and is thus attractive for the user.

Figure 3:
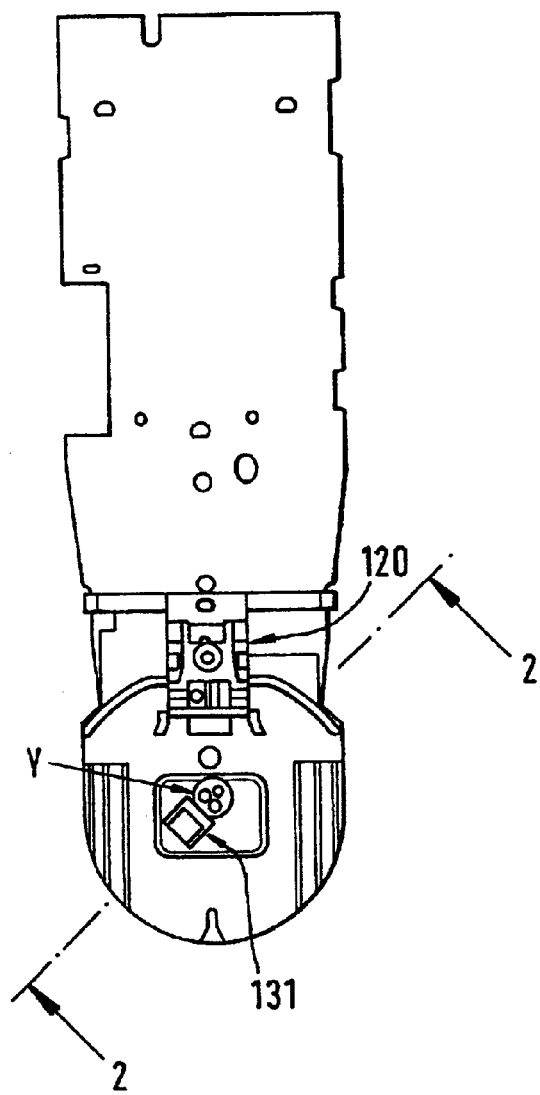
Figure 3:
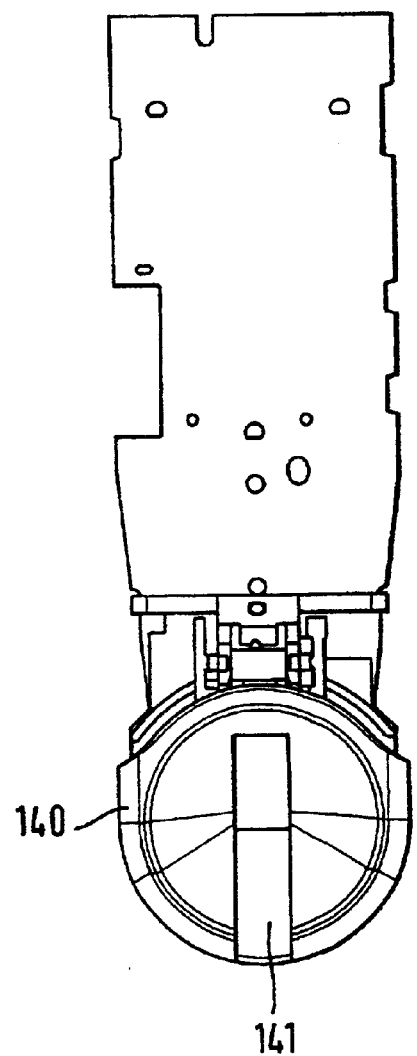

As already mentioned the present invention can be used especially in the field of optical analytical systems which are well-known per se and hence do not require a detailed description here. However, it is worth mentioning that the invention is particularly suitable for analytical instruments in which an analysis is carried out by irradiating an analytical area and evaluating diffusely reflected radiation. Such an instrument optical system is described for example in the document EP 0 819 943, especially in FIGS. 3 to 5 and the accompanying text.

Test elements that are intended to be used in the system according to the invention do not in principle have to have any special properties compared to the known test elements for the above-mentioned instruments of the prior art. However, the present invention is particularly beneficial in the case of test elements that are bendable along their longitudinal axis and are generally referred to as test strips. Such strips have become particularly popular because they are simple and cheap to manufacture and are also simple to handle by the user. They usually have a strip-shaped support made of a flexible plastic. Typical dimensions are for example in the range of 4 cm×7 mm and 1 mm thickness. An analytical area is located on or in this strip which is contacted with sample liquid and yields an optically detectable change which is dependent on the analyte concentration. The construction of such test elements is described for example in the document U.S. Pat. No. 6,036,919. Since the test strip architecture and also the test strip chemistry is well-known in the prior art it is not described in detail here. However, within the scope of the present invention it is important that radiation incident on the test element and preferably also on the analytical area is at least partially specularly reflected. As already mentioned the detection of specularly reflected radiation is used to control the position of the analytical area. It is preferable when the positioning control is carried out directly on the analytical area itself, but if this is not possible because for example the proportion of specularly reflected radiation is too small compared to the proportion of diffusely reflected radiation, then an area of the test element adjacent to the analytical area can be used to check the positioning. This will usually be possible without special measures since the common support materials made of plastic have an adequately high specular reflectivity. However, if necessary the area of the test element which is to be used to check the positioning is prepared by vapour depositing or spattering a reflecting material in such a manner that the position can be easily checked on the basis of specularly reflected radiation. Alternatively it is also possible to select an appropriate material for the test element support. As already mentioned it is usually unnecessary to carry out the positioning control outside the analytical area since the analytical area itself usually has an adequately high specular reflection. Even materials which appear to be diffuse to the observer such as impregnated fleeces, have an intrinsic proportion of specular reflection which is often undesirable for an analytical evaluation of the analytical area with diffusely reflecting radiation. FIG. 1 shows the construction of a test element (10) which is commercially available under the name Glucotrend®. It can be seen that the reagent matrix (14) is located on a transparent foil (13). With this test strip the sample (40) is applied to the upper side and an analytical evaluation is carried out by irradiating the reagent matrix from the underside and detecting diffusely reflected radiation. Hence the area of the support which is optically accessible through the opening (15) represents the analytical area of the test element. Since the foil (13) has specularly reflective properties, this test strip enables a simple control of the positioning using specularly reflected radiation even when the reagent matrix per se has predominantly diffusely reflecting properties. FIG. 1 additionally shows an opening (16) at the distal end of the strip which, as already described is used to hold it. A more detailed description of the test element to which reference is herewith made is given in U.S. Pat. No. 6,036,919.

Figure 2:
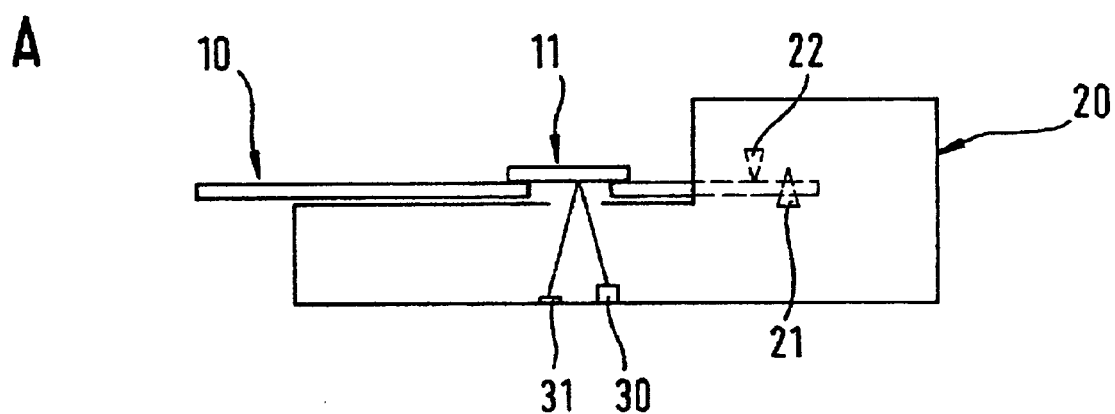
Figure 2:
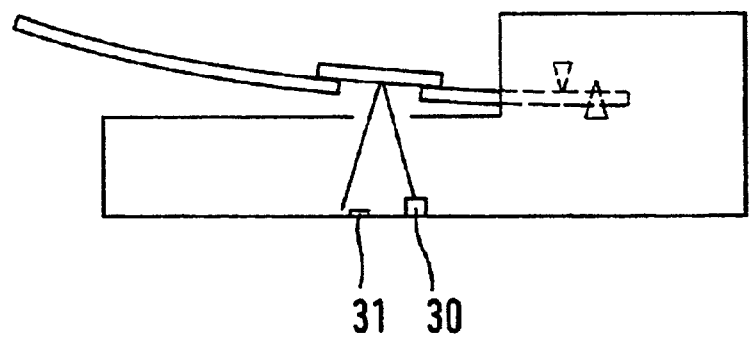

The functional mode of the invention is shown schematically in FIG. 2. The distal end of the test strip (10) is inserted in the analytical unit (20) in such a manner that an opening at the distal end of the test element is held by a pin (21) and the region of the test element proximal to the opening is pressed down by an edge (22). FIG. 2A shows the correct positioning of the test element for evaluation by an analytical unit. The instrument (20) has an opening below the analytical area (11) of the test element through which it is possible to irradiate the analytical area from the underside. The analytical unit which comprises a light source (30) and a detector (31) is located below the opening. Light sources known in the prior art for this purpose are suitable as a light source. In particular it is possible to use light emitting diodes. A semiconductor detector such as a photodiode or a photovoltaic element can be used as the detector (31). As shown in FIG. 2A the light source (30) is arranged such that it illuminates the analytical area (11) at an acute angle to the normal plane. The detector (31) is positioned such that it is impinged by radiation that is specularly reflected from the analytical area. If the strip is removed from its correct position as shown in FIG. 2B which can happen for example when the test element is lifted by the user or the proximal end of the test strip is rested on an object, FIG. 2B shows that the radiation specularly reflected from the analytical area no longer falls on the detector and hence the signal at the detector is smaller than in the case of a correct positioning according to FIG. 2A. The movement of the test element from its correct position can for example be monitored by a quasi continuous monitoring of the signal at the detector (31) and a faulty positioning can be recognized by a signal decrease in a series of measurements. Since such a quasi continuous measurement recording is associated with a relatively high energy consumption, it is preferable to only check the positioning of the test element or the analytical area at a time which is also too close to when the test element is analytically evaluated. In such a procedure a faulty positioning can be detected by comparing the sensor signal with a threshold value, with a blank value without test element or another measured value when the test element is inserted. Other preferred evaluation methods are described in conjunction with a system which also has an optical element for an analytical evaluation of the test element which was omitted in FIG. 2 for reasons of clarity.

FIG. 3A shows a top-view of an instrument board with a test element holder (120) attached thereon and an optical area containing a semiconductor detector (131) and illumination optics (Y) comprising three light-emitting diodes that are directly bonded on the board and lenses above the light-emitting diodes. The illumination optics are illustrated in more detail in conjunction with FIG. 4. FIG. 3B shows the board of FIG. 3A but with an additional removable plastic insert (140). Insert (140) has a groove (141) to receive test elements and to laterally guide the test elements. The combined action of the said lateral guide and the test element holder (120) which engages in an opening of a test element as shown schematically in FIG. 2 ensures that the test element is held laterally. The present invention primarily concerns the detection of vertical deviations in position. If a test element is located in the test element holder of FIG. 3B it may happen that the end of the test element protruding from the instrument is lifted and the analytical area of the test element is removed from the evaluation optics due to inattentiveness or systematic operating errors. The instrument optics acting in conjunction with a suitable evaluation unit is used to detect such a positional deviation and to analytically evaluate a test element.

Figure 4:
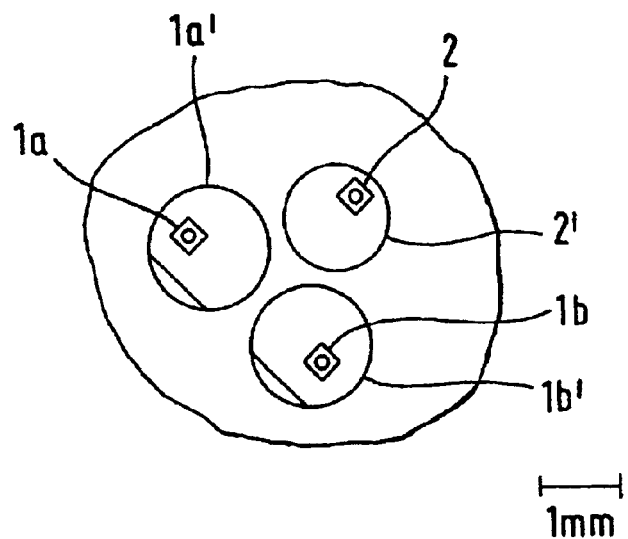
Figure 5:
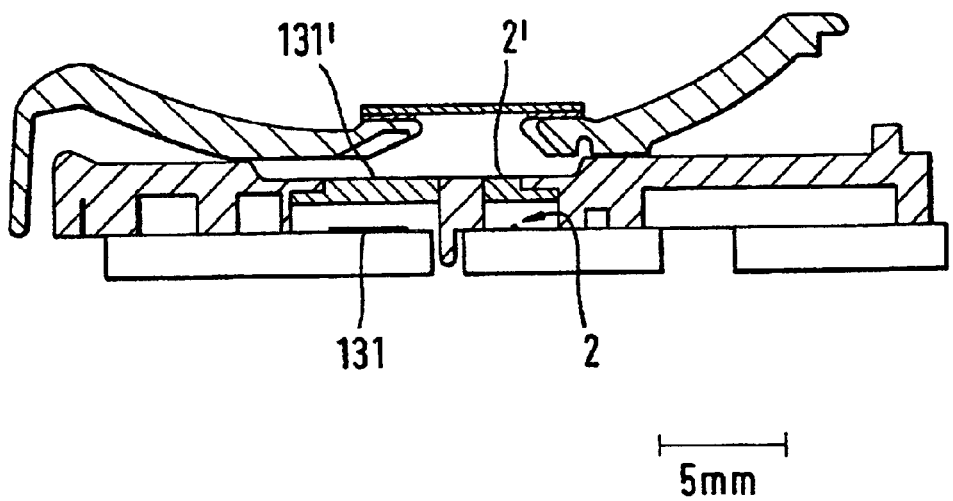

FIG. 4 shows the section (Y) from FIG. 3A which shows the light emitting diodes and the lenses (1a', 1b', 2') above them. FIG. 4 also shows the dimensions which illustrate the high degree of miniaturization of the analytical system. FIG. 4 shows three light sources of which two light emitting diodes (1a and 1b) are at the same distance from the detector (131). These light-emitting diodes are used for the analytical evaluation of the test element and to detect whether an adequate amount of sample has been applied sufficiently homogeneously on the analytical area. This functionality referred as underdosing detection is described in the European Patent Application EP A 0 819 943. The geometric arrangement of the light emitting diodes and the detector relative to one another is such that only diffusely reflected radiation from the underside of the analytical area arrives at the detector. In contrast the light emitting diode 2 is used to check the positioning and is arranged such that when the analytical area is correctly positioned i.e. when the test strip rests on the bottom surface of the groove (141) no specularly reflected radiation falls on the detector. If, in contrast, the end (proximal end) of the test element which is not fixed is lifted, then an increasing amount of specularly reflected radiation falls on the detector and the signal increases. The geometric arrangement of the units is shown in more detail in FIG. 5 as a section through the line 2—2 in FIG. 3A. The light source 2 is only shown as a small black dot in FIG. 5 which is located below the lens 2'. The detector (131) is easier to recognize due to its larger dimensions. The area between the detector and light source is made of black plastic in order to serve as a light trap. In addition an optical window (131') which limits the solid angle for incident light is located above the detector (131).

Figure 6:
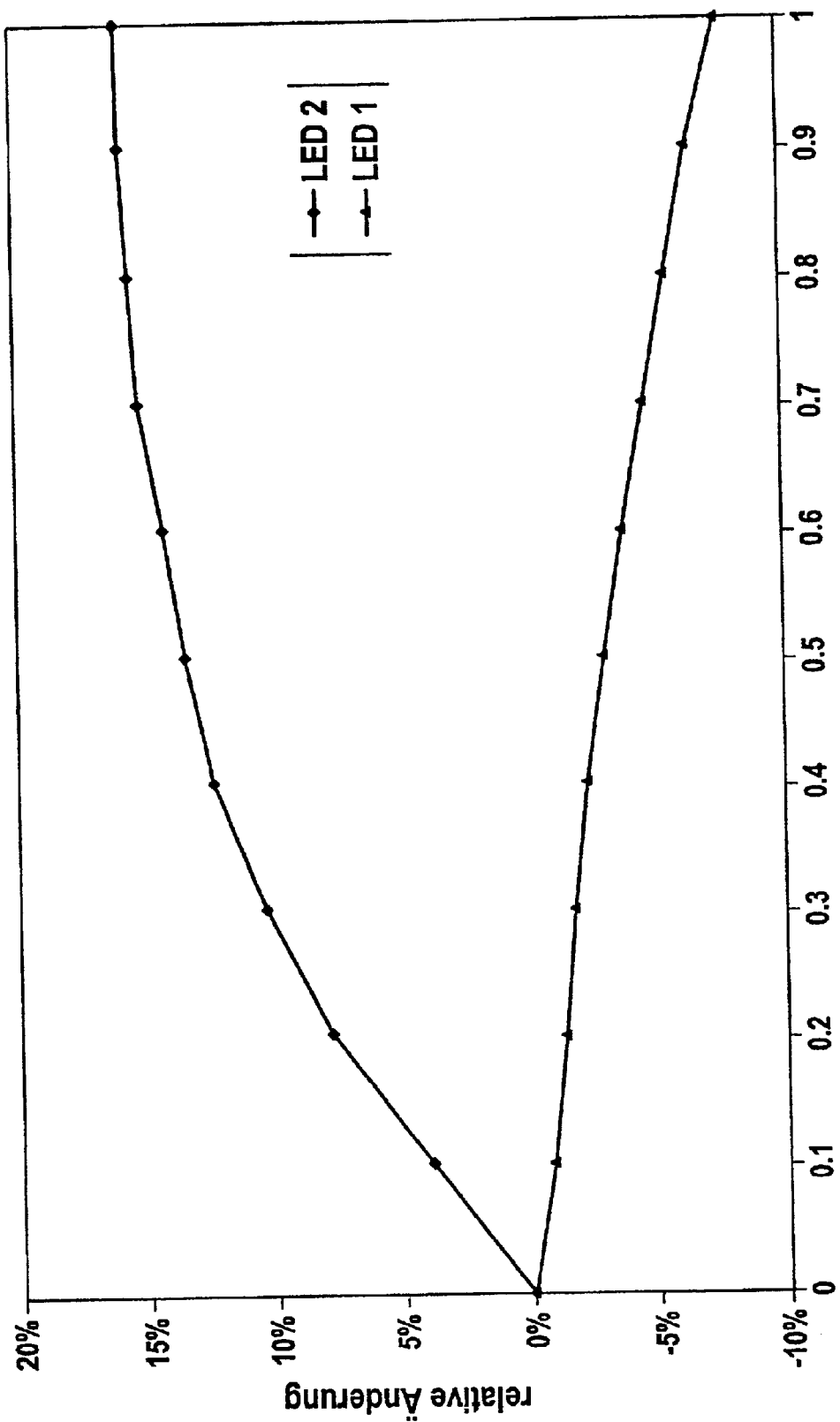

FIG. 6 shows the relative reflectance which is obtained at the detector (131) when the various light emitting diodes are activated in relation to the distance between the supporting surface of the test element (i.e. the bottom of the groove (141) and of the analytical area). The said distance is plotted in mm on the abscissa. The quotient between the intensity at the detector at a given distance is shown on the ordinate for a correct positioning. The upper curve marked by the rhombi represents the quotients of the signals for the light emitting diode 2 for position detection. As shown the quotient and hence also the signal intensity increases when the analytical area is removed from the correct position. As already illustrated by FIG. 5 this is due to the fact that the proportion of specularly reflected radiation incident on the detector increases. The lower curve which is marked by triangles represents the quotients of the previously described signal values when the light emitting diode 1a is activated. It can be seen that the quotient and hence also the intensity decreases when the analytical area is removed from the optical unit. This effect is due to the fact that there is a decrease in the solid angle from which the detector receives radiation. It has proven to be particularly advantageous to calculate the difference between the intensity obtained from the light emitting diode 2 and the intensity obtained from the light emitting diode 1 in order to detect a faulty positioning of the test element or a lifting of the test element from the support. This difference which can also advantageously incorporate relative intensities is even more sensitive to a change in position than the signal from the light emitting diode 2 alone.

In order to carry out a position check the light emitting diodes 1a, 1b and 2 are activated in sequence. This can be carried out by a microprocessor controlled control unit which can also serve as an evaluation unit for the intensity values obtained from the detector. In order to check the positioning the light source 2 is activated and the intensity signal present during this time interval is stored. A more advantageous operating mode than a constant time mode is one in which a frequency is superimposed on the control signal for the light emitting diode and the signal received at the detector is evaluated by means of lock-in amplifier in order to eliminate influences by surrounding light. A position check is especially important at two time points of the analysis. One time point is the measurement of the blank value. In this case the position check ensures that the blank value is not falsified by a movement of the analytical area away from the measuring optics. In such a case the measuring instrument would use a false blank value for the analytical evaluation and/or the timing of the remaining measuring process would be incorrect.

After the measurement of the blank value, the test field is monitored for a time-dependent change of the signal (e.g. one measurement every second). If this signal changes, it is usually assumed that a sample has been applied (or that the test strip has been removed in the case of sample application outside the instrument) and a switch is made to a monitoring of kinetics.

The kinetic monitoring is based on the fact that the observed signals are signals which change with time since usually a chemical reaction with a particular kinetics occurs in the analytical field after the sample liquid has been applied. This change with time is detected by a continuous measurement or measurements carried out at intervals (typically between 2 s and 0.5 s). In the case of a blank value measurement a detection/control of the position is also important in order to prevent a start of the kinetic monitoring due to a change in the position of the test element although no sample has yet been applied. This would lead to completely false results.

The second critical point is the analytical evaluation per se which is preferably triggered when the time-dependent signal change at the detector falls below a specified threshold value when illuminated with LED 1a or 1b. If this is the case the actual analytical measurement is initiated for which successive measurements are made with light sources 1a and 1b and preferably a mean of the detector signals is used for the evaluation. In a very short time interval i.e. preferably in a time interval of less than 1 second a position detection is carried out in order to ensure that the detector signals have been recorded during a correct positioning of the test element. Furthermore measurements with a long intervening time interval can result in a falsified analytical result since the chemical reaction in the analytical area proceeds further.

If a faulty positioning is detected during the measurement of the blank value or during the analytical evaluation the instrument displays an appropriate error message. The instrument preferably indicates the faulty positioning by an appropriate message in a display or an acoustic signal so that the user can eliminate the faulty positioning. Hence a suitable control of the measuring cycle can in many cases prevent the measurement and also the test element and sample from being discarded.

What is claimed is:

1. A system for analyzing sample liquids by evaluating test elements with an analytical unit in which a test element to be analyzed is positioned by a holder in an analytical position relative to the analytical unit, the system comprising, a position control unit to check whether an analytical area of the test element is correctly positioned relative to the analytical unit wherein the position control unit comprises:
   (a) a light source to irradiate an area of the test element,
   (b) a detector to detect light reflected from the area, and
   (c) an evaluation unit, wherein the light source and detector are positioned relative to one another in such a manner that the light intensity of specularly reflected radiation from the test strip at the detector when the test element is correctly positioned is different from the light intensity of reflected radiation from the test element at the detector when it is incorrectly positioned, and the evaluation unit is adapted to recognize any faulty positioning on the basis of the light intensity at the detector.

2. The system of claim 1, in which the light source and detector are arranged relative to one another in such a manner than when the test element is correctly positioned, specularly reflected radiation falls on the detector and the proportion of specularly reflected radiation decreases when a faulty positioning occurs.

3. The system of claim 2, in which the proportion of specularly reflected radiation of the light source for position control decreases at the detector when a faulty positioning occurs.

4. The system of claim 1, in which the light source and detector are arranged relative to one another in such a manner that when the test element is correctly positioned, the proportion of radiation specularly reflected from the test element is small or zero and is larger when the test element is incorrectly positioned.

5. The system of claim 1, in which the analytical unit is used to irradiate the analytical area and the concentration of an analyte is determined on the basis of the radiation reflected from the analytical area or transmitted through the analytical area.

6. The system of claim 5, in which the analytical unit uses the detector of the position control unit to detect radiation.

7. The system of claim 5, in which the analytical unit uses the light source of the position control unit to irradiate the analytical area.

8. The system of claim 1, in which the test element is deformable along its longitudinal axis, is held in an area at one end of the axis by a holder and the analytical area is at a distance from said one end of the axis such that a faulty positioning of the analytical area relative to the analytical unit occurs when the test element is bent along its longitudinal axis.

9. The system of claim 1, in which the analytical unit has a measuring light source and a control unit sequentially actuates the measuring light source and the light source of the position control unit.

10. The system of claim 9, in which the measuring light source irradiates the analytical area below an angle of a and the light source of the position control unit irradiates the analytical area below an angle of $\beta$ relative to the normal plane whereby $\alpha<\beta$.

11. The system of claim 1, in which the position control unit comprises a second light source which is positioned relative to the detector in such a manner that at the detector the light intensity of this radiation reflected from the test element changes inversely to the light intensity of the light source for position control when the test element is moved away form its correct position.

12. A method for analyzing sample liquids comprising evaluating test elements using an analytical unit in which a position control unit is used to check whether an analytical area of the test element is positioned correctly relative to the analytical unit, irradiating an area of the test element by a light source, detecting radiation reflected from the area, recording a signal generated by the detecting step to check the position of the analytical area wherein the light source and detector are positioned relative to one another in such a manner that the intensity of radiation reflected from the test element and detected is different when the analytical area is correctly positioned than the intensity when it is incorrectly positioned, and indicating to a user whether the analytical area is positioned correctly relative to the analytical unit.

13. The method of claim 12, in which the analytical unit has a separate light source and a detector is used for the detecting step and the light source of the position control unit is actuated at a time point $T_K$ and the light source of the analytical element is actuated at a time point $T_A$ and the position of the analytical area is checked on the basis of the signal generated by the detector at time point $T_K$ and an evaluation to determine the concentration of an analyte is carried out based on the signal generated at time point $T_A$.

14. The method of claim 13, in which the time points $T_K$ and $T_A$ are les than one second apart.

* * * * *

UNITED STATES PATENT AND TRADEMARK OFFICE
CERTIFICATE OF CORRECTION

PATENT NO. : 6,906,802 B2
DATED : June 14, 2005
INVENTOR(S) : Dirk Voelkel

It is certified that error appears in the above-identified patent and that said Letters Patent is hereby corrected as shown below:

Column 8,
Line 18, please replace "a" with -- α --.
Line 28, please replace "form" with -- from --.
Line 53, please replace "les" with -- less --.

Signed and Sealed this

Thirtieth Day of August, 2005

JON W. DUDAS
*Director of the United States Patent and Trademark Office*